(12) United States Patent
Beyrard

(10) Patent No.: US 7,460,217 B2
(45) Date of Patent: Dec. 2, 2008

(54) DEVICE FOR DETERMINING A REFRACTIVE INDEX IN A LARGE NUMBER OF POINTS OF A PHYSICAL ENVIRONMENT

(76) Inventor: Norbert Beyrard, 170, avenue des Thermes, Divonne-les-Bains (FR) F-01220

( * ) Notice: Subject to any disclaimer, the term of this patent is extended or adjusted under 35 U.S.C. 154(b) by 36 days.

(21) Appl. No.: 11/610,636

(22) Filed: Dec. 14, 2006

(65) Prior Publication Data
US 2007/0085999 A1    Apr. 19, 2007

Related U.S. Application Data

(63) Continuation of application No. PCT/FR2005/001436, filed on Jun. 10, 2005.

(30) Foreign Application Priority Data

| Jun. 16, 2004 | (FR) | ................................. | 04 06497 |
| Nov. 18, 2004 | (FR) | ................................. | 04 52677 |
| Apr. 1, 2005 | (FR) | ................................. | 05 03183 |

(51) Int. Cl.
*G01N 21/41*    (2006.01)
(52) U.S. Cl. .................................. 356/128; 356/131
(58) Field of Classification Search .................. 356/128, 356/131
See application file for complete search history.

(56) References Cited

U.S. PATENT DOCUMENTS

| 4,792,227 A | * | 12/1988 | Yoshizawa .................. 356/128 |
| 5,588,032 A | | 12/1996 | Johnson |
| 5,633,708 A | | 5/1997 | Svendsen |

FOREIGN PATENT DOCUMENTS

WO    WO03042670    5/2003

\* cited by examiner

*Primary Examiner*—Roy M Punnoose
(74) *Attorney, Agent, or Firm*—Sturm & Fix LLP

(57) ABSTRACT

A device for determining a refractive index (Rl) in a large number of points of a physical medium, comprising: a light laser for performing a series of p pulsed laser rays (PLRs) each proceeding from a starting point Ap and arriving in an arrival point Bp following the shortest optical path between the two points Ap and Bp; a timer to record a time Tp when each PLR reaches the arrival point Bp; and a computer programmed for finding the shortest optical path among all the optical paths starting from the starting point Ap and all reaching the arrival point Bp, and from p linear equations linking elementary optical paths (L) and the refraction indices (N) to the detected travel time Tp, for solving the matrix equation [N]*[L]=[T] relative to a vector of the refractive indices [N] and repeating until [L] and [N] converge.

16 Claims, 5 Drawing Sheets

DEVICE FOR DETERMINING A REFRACTIVE INDEX IN A LARGE NUMBER OF POINTS OF A PHYSICAL ENVIRONMENT

CROSS REFERENCE TO RELATED APPLICATIONS

This application is a continuation of PCT/FR05/001436 filed Jun. 10, 2005, which claims priority of Application Nos. FR 0406497 filed Jun. 16, 2004, FR0452677, filed Nov. 18, 2004, and FR0503183, filed Apr. 1, 2005, which are all incorporated by reference herein in their entirety.

BACKGROUND OF THE INVENTION

1. Field of the Invention

The present invention relates to an apparatus for determining a refractive index in a large number of points p, for example 10000 points, of a physical medium.

2. Description of the Related Art

The use for example of an infra-red laser scanner raises the problem of investigating the optical path when the infra-red beam passes through a medium consisting of layers of different refractive indices. Often the approach is to ignore the refractive index of all the points through which the beam passes.

SUMMARY OF THE INVENTION

To this end the invention provides an apparatus for determining a refractive index in a large number of points p, for example 10000 points, of a physical medium, each point being defined by a fixed reference point occupying the centre of gravity of an elementary grid unit or block, in which p elementary grid units form a grid-like array of the physical medium, characterised in that the apparatus comprises:

a light laser, for example an infra-red laser, displaceable in elementary steps along a displacement guide or fixed with respect to a mirror displaceable in elementary steps along the displacement guide, in order to carry out a series of p coplanar "shots" each starting from a starting point Ap defined with respect to the displacement guide and arriving at an arrival point Bp defined by a detection means, after having passed through the physical medium along an optical path defined as being the shortest optical trajectory between the two points Ap and Bp;

a counter time-synchronised with each shot so as to record an instant Tp when each shot reaches the arrival point Bp counting from the initial instant when the shot has left the starting point Ap; and a computer suitably programmed to carry out the following steps:

(1) to investigate the optical path from among the optical trajectories all leaving from the starting point Ap and all arriving at the arrival point Bp, each optical trajectory being defined by a sequence of elementary optical paths (L) each equal to the arithmetic product of two terms, in which the first term is a modulus of a vector connecting two centres of gravity of two adjacent elementary grid units, and in which the second term is an estimated refractive index at each centre of gravity;

(2) starting from p linear equations connecting, for each of the p investigated optical paths, the elementary optical paths (L) and the indices of refraction (N) to the detected passage time Tp, to construct a square matrix of the elementary optical paths [L], a vector of the refractive indices of the elementary grid units [N] and a vector of the passage times of the light ray [T] and to solve the matrix equation;

$$[N]*[L]=[T]$$

with respect to the vector of the refractive indices of the elementary grid units [N]; and (3) to repeat the steps (1) and (2) so as to investigate new optical paths with the refractive indices of the elementary grid units calculated during an immediately preceding iteration, to solve the matrix equation with the new elementary optical paths corresponding to the new investigated optical paths and obtain a new vector of the refractive indices of the elementary grid units until the matrix of the elementary optical paths [L] converges and the vector of the refractive indices of the elementary grid units [N] also converges.

Advantageously, the apparatus is characterised in that, in order to determine a coefficient of attenuation at any point of the physical medium where a refractive index has been determined:

the detection means is adapted so as to detect a variation of intensity ($\Delta$Ip) of each shot of the series between the starting point Ap and the arrival point Bp taking into consideration an attenuation of the light intensity along the elementary optical paths followed by each shot, which is a function of a coefficient of attenuation E associated with each elementary grid unit; and the computer is suitably programmed so as to carry out the following supplementary step:

(4) starting from p linear equations connecting the elementary optical paths (L) for which the vector of the refractive indices of the elementary grid units has converged in stage (3) and the coefficients of attenuation (E) of the elementary grid units (100) to the variation in intensity ($\Delta$Ip) of each of the p shots of the series, to construct a vector of the coefficients of attenuation of the elementary grid units [E] and a vector of the variations of intensity ($\Delta$Ip), and then by a mathematical method involving linear algebra to solve the matrix equation:

$$[E]*[L]=[\Delta Ip]$$

with respect to the vector of the coefficients of attenuation of the elementary grid units [E].

Preferably the computer carries out stage (1) by being suitably programmed to investigate the optical path by a method involving the calculation of a minimal critical path from estimates of the refractive indices obtained by an imaging method using an X-ray scanner, a nuclear magnetic resonance imaging unit, or also an echography unit.

In an embodiment of the invention the apparatus is characterised in that, in order to arrive at an estimate of the refractive indices with a greater spatial resolution with respect to the physical medium:

the displacement guide is provided with a micro-actuator displacing the light laser or the mirror along the displacement guide by an elementary micro-step equal to the elementary step divided by an amplification factor K so as to carry out two crossed series of shots X and Y respectively, both coplanar and each starting from a starting point Ax or Ay defined with respect to the displacement guide and arriving at an arrival point Bx or By defined by the detection means after having passed through the physical medium along an optical path defined as being the shortest optical trajectory between the two points Ax and Bx or Ay and By, and the computer is suitably programmed to carry out the following supplementary stages:

(5) to investigate the optical path among a large number of optical trajectories all starting from the starting point Ax or Ay and all arriving at the arrival point Bx or By, being defined by a sequence of micro-elementary optical paths (μL) each equal to the arithmetic product of two terms, in which the first term is a modulus of a vector connecting two centres of gravity of two adjacent elementary micro-grid units and in which the second term is a refractive index (N') at each centre of gravity of each elementary micro-grid unit equal to the refractive index of the elementary grid unit from which the elementary micro-grid units are derived after division by the amplification factor K and for which the vector of the refractive indices of the elementary grid units [N] has converged in (3), and from K*p=X+Y linear equations connecting, for each of the investigated optical paths of one series X and the other series Y of the two series of shots, the micro-elementary optical paths (μL) and the refractive indices of the elementary micro-grid units (N') to the passage time Tx or Ty detected by means of the computer time-synchronised with each shot reaching the arrival point Bx or By counting from the initial instant when the shot left the starting point Ax or Ay, to construct a square matrix of the micro-elementary optical paths (μL), a vector of the refractive indices of the elementary micro-grid units [N'] and a vector [T] of the passage times of the light ray, and then (6) to adjust the refractive index in each elementary micro-grid unit by a method of least squares taking into account constraints imposed by the boundary values set by the detected passage times Tx or Ty, using the following formula:

$$Cij = Bij + \left(\frac{1}{n}\right) * \left(pj - \sum_{1}^{n} Bij\right) + \left(\frac{1}{m}\right) * \left(ci - \sum_{j=1}^{m} Bij\right) - \left(\frac{1}{nm}\right) * \left(\sum_{j=1}^{m} \rho j - \sum ijBij\right)$$

where, in this formula,

Cij is the sought value

Bij is the initially estimated value (n) is the number of lines of a representative matrix of a table of the refractive indices of the micro-elementary grid units (n>X)

(m) is the number of columns of a representative matrix of a table of the refractive indices of the micro-elementary grid units (m>Y)

$$\sum_{i=1}^{n} Cij$$

=pj for all the values of i, the constraint of the column j.

$$\sum_{j=1}^{m} Cij$$

=ci for all the values of j, the constraint of the line i.

Advantageously the apparatus is characterised in that, in order to make an estimate of the coefficients of attenuation with a larger spatial resolution with respect to the physical medium:

the computer (106) is suitably programmed to carry out the following supplementary steps:

(7) starting from a variation of intensity (Δlx, Δly) detected by the detection means for each shot of the two crossed series of shots X and Y between the starting point Ax or Ay and the arrival point Bx or By taking into consideration an attenuation of luminous intensity along the micro-elementary optical path followed by each shot, which is a function of a coefficient of attenuation (E') affecting each elementary micro-grid unit and equal to the coefficient of attenuation (E) of the elementary grid unit from which the elementary micro-grid units are derived, divided by the amplification factor K, and from K*p=x+Y linear equations connecting, for each of the investigated optical paths of one series X and the other series Y of the two series of shots, the micro-elementary optical paths (μL) and the coefficients of attenuation of the elementary micro-grid units (E') to the variations of luminous intensity (Δlx, Δly), to construct a square matrix of the micro-elementary optical paths (μL), a vector of the coefficients of attenuation of the elementary micro-grid units [μE'] and a vector (Δl) of the variations of luminous intensity; and (8) to adjust the coefficients of attenuation in each elementary micro-grid unit by a method of least squares taking into account constraints imposed by the boundary values that form the detected variations in luminous intensity Δlx or Δly, using the following formula:

$$Cij = Bij + \left(\frac{1}{n}\right) * \left(pj - \sum_{1}^{n} Bij\right) + \left(\frac{1}{m}\right) * \left(ci - \sum_{j=1}^{m} Bij\right) - \left(\frac{1}{nm}\right) * \left(\sum_{j=1}^{m} \rho j - \sum ijBij\right)$$

where, in this formula,

Cij is the sought value

Bij is the initially estimated value (n) is the number of lines of a representative matrix of a table of the coefficients of attenuation of the micro-elementary grid units (m) is the number of columns of a representative matrix of a table of the coefficients of attenuation of the micro-elementary grid units $$\sum_{i=1}^{n} Cij$$

=pj for all the values of i, the constraint of the column j.

$$\sum_{j=1}^{m} Cij$$

=ci for all the values of j, the constraint of the line i.

In the particular case where the physical medium is a part of a human or animal body and in order to treat a singularity of the refractive indices representative of a tumour or another pathological condition of a part of this body, the apparatus is characterised in that:

the apparatus comprises a pulse-type treatment light laser in order to generate a beam of very short duration, for example 100 femtoseconds, and with a very high energy, mounted on the displacement guide and provided with a displaceable lens so as to adjust a focal length along a neutral axis of the lens and to cause the beam to converge at the focal point of the neutral axis; and the computer is suitably programmed to carry out the following supplementary steps:

(9) to search for a singularity C among the refractive indices calculated on completion of step (3) or adjusted on completion of step (6) or among the coefficients of attenuation calculated on completion of step (4) or adjusted on completion of step (8), and to define by referencing the grid units or the elementary micro-grid units of the singularity C with respect to the displacement guide, and

(10) to investigate, for a plurality of points of the lens, the optical path between a starting point Aq and the singularity C regarded as the point of arrival, and to calculate an angle of convergence averaged over the various investigated optical paths starting from different points of the lens and obeying a symmetry condition with respect to the beam, so as to adjust the focal length to a virtual focal point determined by the angle of convergence assuming that the beam travels in air, in such a way as to focus the said beam on the virtual focal point so that the singularity C coincides with a real focal point in order to be destroyed, for example by vaporisation, under the action of repeated pulses of the light laser.

BRIEF DESCRIPTION OF THE DRAWINGS

Other advantageous characteristics of the invention are described by means of several embodiments and with the aid of the following diagrams, in which.

DETAILED DESCRIPTION OF THE PREFERRED EMBODIMENT

The apparatus according to the invention implements a method for calculating the optical path and its applications to the detection of objects, in particular in an aqueous medium, or to the implementation of a tomodensitometric method disclosed hereinafter. In fact, the use of infra-red radiation, coherent or otherwise, passing through heterogenous media assumes that the optical path in this medium can be traced. This furthermore assumes a knowledge of the refractive indices at all the points of the medium under investigation, and a knowledge of the possible, total or partial reflection or reflections during the course of the projectory.

Experimenters are thus confronted with various cases. In the first case the traversed medium and the refractive index at each point are known. In the second case only incomplete information is available.

In the first case two methods may be used to calculate the optical path, that which uses DESCARTES' second law or a method using the principles formulated by FERMAT if the refractive index is known at all points.

DESCARTES' second law concerning refraction expresses the deviation of a light ray passing through an interface between two media, by the relationship shown below, in which the angle of incidence in the medium 1 is connected with the angle of refraction in the medium 2 by the following equation:

$$n_2 \sin i_2 = n_1 \sin i_1$$

in which:

n1 is the refractive index and i1 is the angle of refraction of the first medium n2 is the refractive index and i2 is the angle of refraction of the second medium FERMAT's principle may also be used to calculate the optical path between two points. In fact, FERMAT's principle may be stated in the following way: any trajectory followed by a radiation corresponds to a stationary optical path such that the sum of the elementary optical paths is a minimum. An elementary optical path is the arithmetic product of the length of the vector connecting two points, and the refractive index of the medium through which the radiation passes.

More generally, the optical path between a point A and a point B may be written in the following way:

$$L = \int_A^B n \, ds$$

It will be recalled that the optical path is that corresponding to a trajectory, among the various possible trajectories, such that the sum of the consecutive elementary optical paths constituting the said trajectory is a minimum. Each of the elementary optical paths is equal to the arithmetic product of the geometrical distance between the ends of the vector and the refractive index of the traversed medium.

The author of the present invention has devised an original method in order to calculate the optical path, using a process that enables not the longest path but instead the shortest trajectory to be calculated using a graph of vectors connecting different points.

Figure 1:
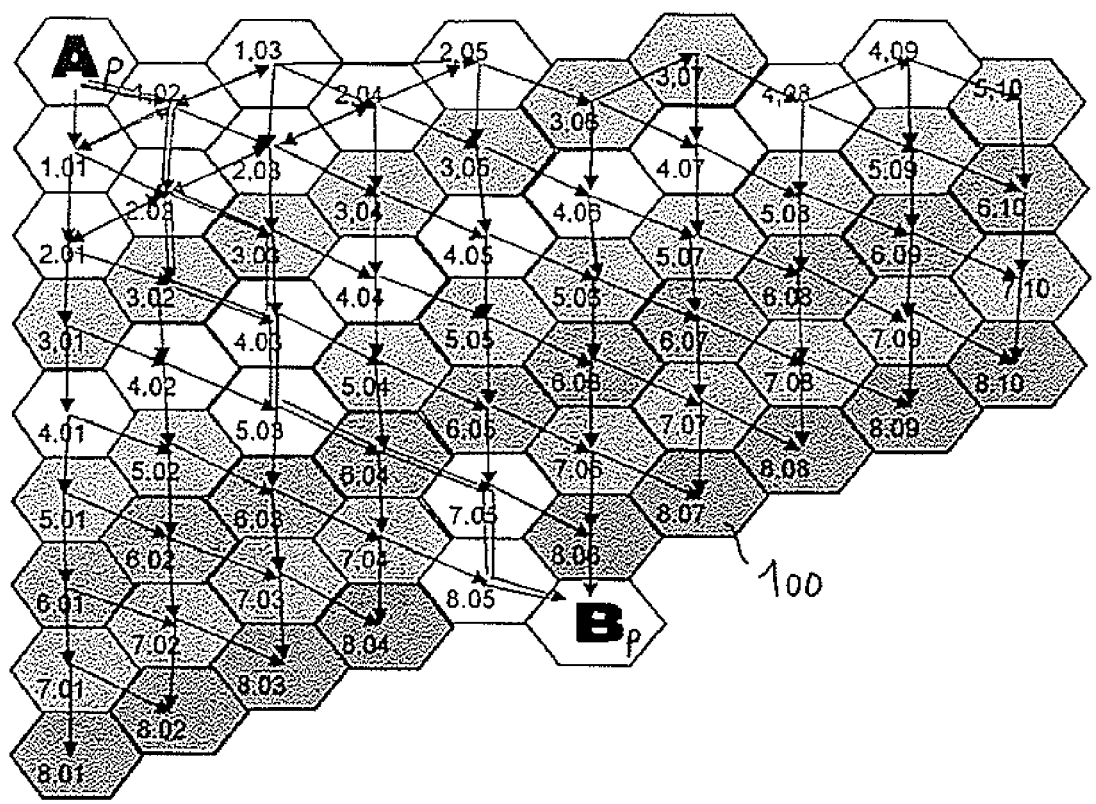
FIG. 1 shows points in a physical medium, each point occupying the centre of gravity of an elementary grid unit, in which the elementary grid units form a grid-like ray of the physical medium.

In the case of a more complex situation, for example that shown in FIG. 1, only the starting point and the arrival point of the ray are known and Fermat's principle can be used to plot the optical path. The use of this principle is possible by utilising the method of the critical path, which enables a trajectory to be calculated within the framework of a network of vectors connecting different points, for example a point A to a point B. In this case the critical path method enables the longest path to be calculated, which may be obtained by replacing the trajectory elementary vector by a vector equal to an over-estimate minus the trajectory elementary vector, as follows:

to go for example from the point A to the point 1.2 (in the centre of the layer 1 of the graph of FIG. 3), the elementary trajectory will be equal to:

$$M-0.5\, L_1 * 1.003 - 0.5\, L_{1,2} * 1.003$$

to go from the point 1.1 to the point 2.3, the elementary trajectory will be equal to:

$$M-0.5\, L_2 * 1.003 - 0.5\, L_{2,3} * 1.333$$

The critical path method will thus determine the shortest trajectory for values of Lij, that is to say the traversal distance of each hexagonal element shown on the graph of FIG. 1.

It is possible to replace the process for calculating the critical path by a method for calculating the minimum path. The advantage relating to the use of the critical path method is that suitable software is available.

Since 1965 the inventor has developed and perfected a process for determining the critical path by a method of antecedents, the TELOR method. In the context of the present invention this method can be used to plot directly an optical path by referring step by step to the minimum value of the specified antecedents.

With reference to the graph shown in FIG. 1, starting from the point A three vectors may be plotted, terminating at the points 1.01, 1.02 and 1.03. The shortest path starting from A terminates at the point 1.02, since its length is equal to 1.003. On going to the next stage, namely going from the layer 1 to the layer 2, we have plotted 9 vectors, starting from the points 1.01, 1.02 and 1.03, which gives us the path starting from the origin and going to any of the indicated points, by adding to the value of the vector (length), the values of the antecedent vectors. For example, the vector 8, which goes from the point 1.02 to the point 2.02, has two antecedents, namely the vectors 2 (A, 1.02) and 4 (1.01, 1.02). The shortest length is that corresponding to 2.02, which is found on the optical path of the sought trajectory.

Figure 3:
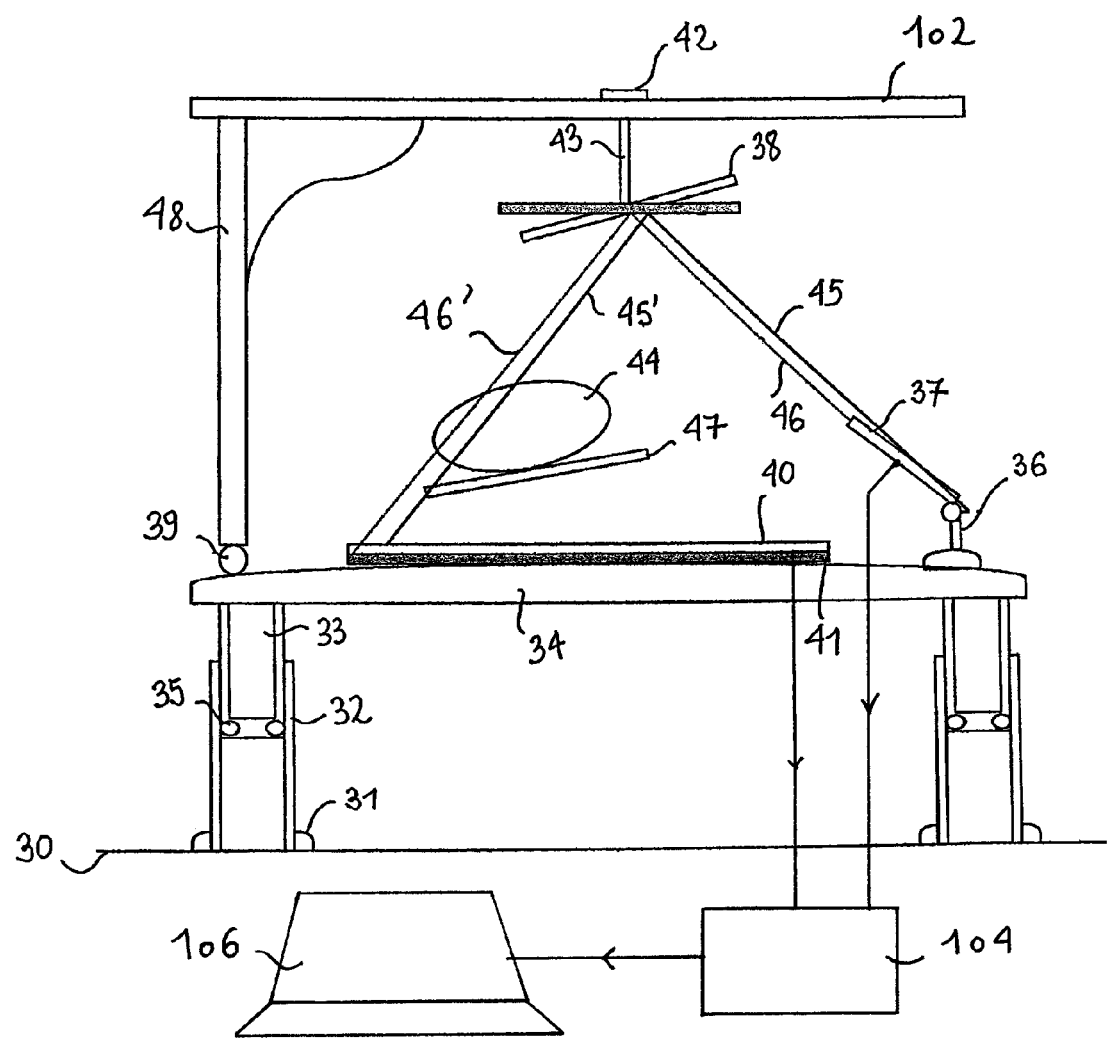
FIG. 3 is a plan view of an apparatus according to a first embodiment of the invention.

By proceeding in this way step by step from the vector A to the vector B, the optical path will be determined, which moreover in our example includes a divergence, which is plotted in FIG. 3. The two optical paths are thus the following:

A, 1.02, 2.02, 3.02, 4.03, 5.03, 6.04, 7.05, 8.05, B
A, 1.02, 2.02, 3.03, 4.03, 5.03, 6.04, 7.05, 8.05, B

This example shows that when a completely coherent medium is traversed, which is the case for the layer No. 3, the optical path may take two different routes, even if a coherent light is involved.

Figure 2:
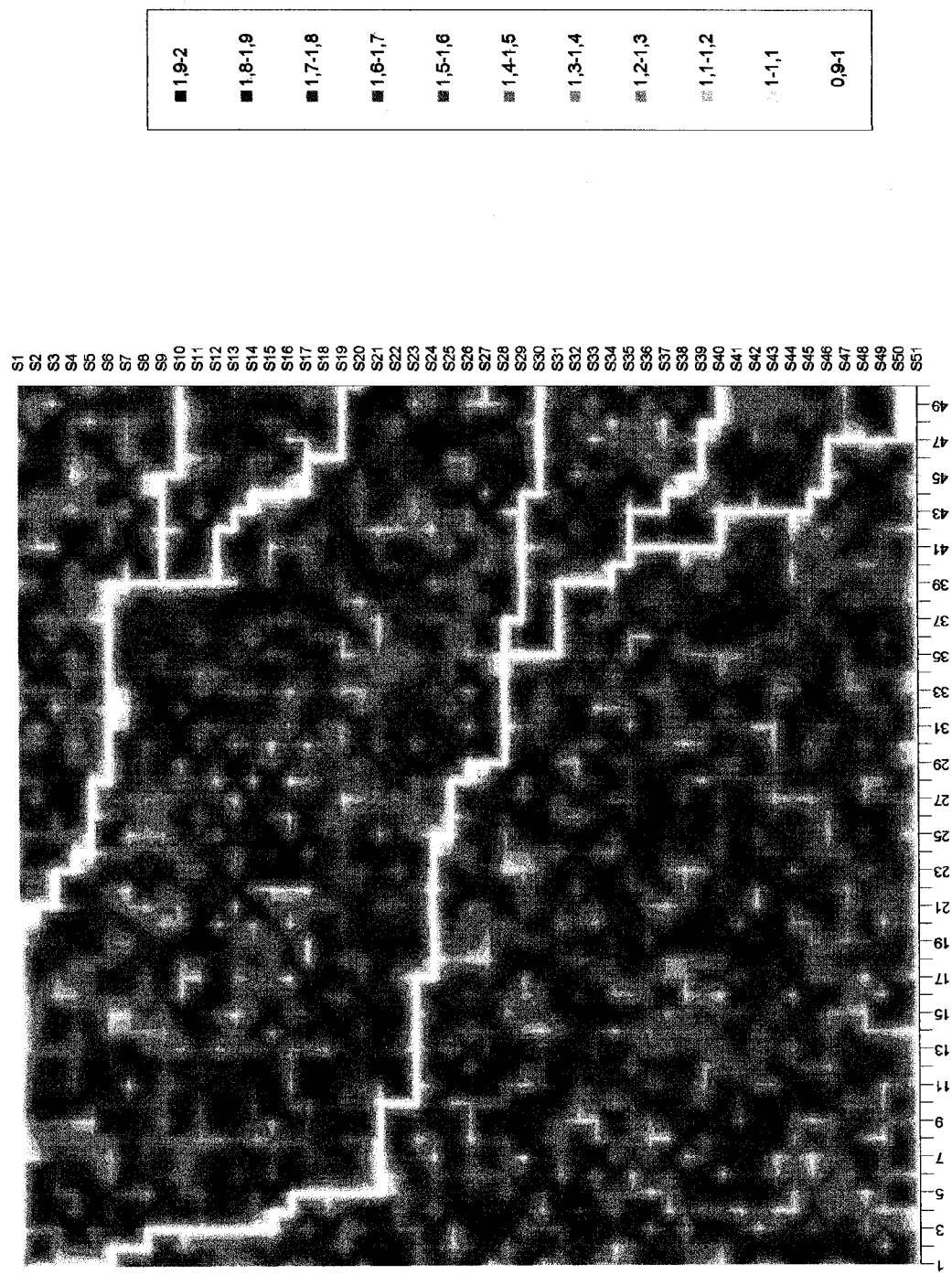
FIG. 2 shows graphically a square matrix of 10000 points of refractive indices varying randomly between 1 and 2, and five optical paths between a starting point and five arrival points.

The system also enables us to start from a point and to plot a large number of paths, corresponding for example to scannings of the laser ray, as illustrated in FIG. 2.

However, it often happens that the refractive index of all the points of the traversed medium is ignored. In this second case, an apparatus according to the invention is employed in the following way:

1/ an evaluation of the nature of the medium is carried out, for example by means of a first examination using for example an X-ray scanner with a low definition of the order of 1 mm.

2/ the densitometric plane is sliced, either into squares of size 100 microns for example, or in a more sophisticated way by a hexagonal grid-like arrangement as shown in the diagram of FIG. 1.

3/ thanks to a knowledge of the constituent substances of the traversed medium, an estimate of the refractive index for each of the squares or each of the hexagonal elements is obtained.

4/ a graph is plotted going from the point A to the point B and passing through all the centres of the elementary squares or elementary hexagons.

5/ each vector of the graph is allocated a value equal to an over-estimate minus the value of the elementary optical path, or alternatively a direct investigation of the minimum path is carried out.

6/ the critical path of this graph is determined, which is thus equal to the sum of the over-estimates less the sum of the elementary optical paths, the desired optical path thereby being obtained. A procedure involving the direct investigation of the minimum path may also be adopted.

7/ this optical path corresponds to a linear relationship between the elementary optical paths, that is to say the values of the indices of each mini-zone or elementary grid units.

8/ the exercise is repeated for a large number, for example p equal to 10000, starting points Ap and arrival points Bp, and a set of linear relationships interconnecting the values of the sought refractive indices is thereby obtained.

9/ the resulting equation is solved by linear algebra in order to obtain the real value of the indices of each mini-zone.

10/ a first calculation of the refractive indices is thus available.

11/ the operation is repeated until the results obtained are physically satisfactory.

In other words, the apparatus according to the invention implements a method in which it is assumed that information regarding the medium is available that allows the refractive index of all the points of the observed medium to be estimated, a probable optical path between a point A and another point B is calculated, which leads to the establishment of a linear relationship between the indices along the trajectory, these calculations are repeated for a sufficient number of points Ap and Bp, from which one can derive p equations for p points, the refractive indices at p points are calculated, and the operation is repeated until the results converge on the geometric plane.

In fact, in a large number of applications the trajectory of a light ray or optical path has to be calculated in order to check or produce materials intended for optical use, to detect objects or obstacles, or also to produce images.

Thus, in the present invention the author has examined in a general manner how the refractive indices could be obtained when insufficient information is available.

In a first stage an evaluation of the refractive index at each of the points is carried out, for example from a knowledge of the medium provided by an image obtained by an X-ray scanner, IRM (magnetic resonance imaging) or echography. In fact, there is a certain correlation between the coefficient of attenuation at each point shown by the image obtained for example by an X-ray scanner (or otherwise), and the refractive index, insofar as it is possible to define the probable medium to which a certain zone of the image produced by the X-ray scanner corresponds, or by any other internal medical imaging method. It is clear that different human tissues, bone, fat, etc. appear differently in the image.

In a second stage one can determine the trajectory between a point A and a point B, as is shown for example in the hexagonal grid-like array and in the calculation that was used to investigate the optical path in this case. If the preceding formulation is repeated (see page 4, lines 13 to 16), the specified coefficients of 1.003 and 1.333 corresponding to the two supposedly known media may be replaced by unknowns, which would give a relationship along the whole of the optical path that could be written as follows for the p-th shot:

$0.5NA + N1.02 + N2.02 + N3.03 + N4.03 + N5.03 + N6.04 + N7.05 + N8.05 + 0.5B$

By carrying out a simple change of variable and noting that the distance traveled is proportional to the velocity $Vp=K/Np$, which leads to the result that the refractive index is proportional to the passage time $Tp$ of a given distance, a linear relationship may be established between the $Nn$ proportional to the passage time (which is virtually constant), and in the case of a hexagonal grid-like array for the p-th shot $5NA + \ldots + 0.5NB = Tp$ In fact, a velocity of the light corresponds to each refractive index, and the value $Tp$ of the optical path traveled may be calculated from the time taken between A and B. This value Tp is observable, and for example for a length of 10 cm the travel time in air is 0.333 nanosecond, whereas the currently available apparatuses enable femtoseconds to be measured, i.e. times one millionth smaller than a nanosecond.

If one has p optical paths for p points, then the refractive indices at all points can be calculated by linear algebra, provided that the optical paths remain unchanged in each case.

Since one is not sure that the first evaluation is good, the values of the second evaluation will be substituted and the optical paths will be recalculated until the refractive index of a given zone no longer changes in the calculation process or, which is more convenient, it is assumed that a sufficient accuracy has been reached when the sum of the deviations or the sum of the standard deviations indicating the overall variation between two levels of calculation are less than a predetermined threshold value.

It is accepted that if the deviation between the calculated time and the measured time is small, then the physical path is virtually the same. This analysis of the deviation may be carried out if necessary at each stage and allows the calculations to be checked.

One may then proceed by using the algorithm disclosed hereinafter, by carrying out two crossed scanning sequences X and Y, using an infra-red laser (or other light laser). The refractive indices of a micro-zone or elementary micro-grid unit will be evaluated by matrix expansion without dividing by the square of the refractive indices of the elementary zone or grid unit, but instead taking the value of the index of the mini-zone as that of the zone.

The principles of division by the expansion factor K will again be adopted for the coefficient of attenuation.

Assuming to a first approximation that the optical paths may be determined on the basis of evaluated refractive indices, the evaluated refractive indices will be corrected in order to minimise the squared deviations between the initially estimated refractive index and the re-estimated refractive index, taking into account constraints imposed by the real trajectory.

One may in this case also complete the analysis by taking into account once more the refractive indices or the attenuations as described above, by following a two-stage process:

1/ a stage involving a large definition (for example 1 mm)

2/ a stage involving a finer definition (for example 10 microns)

The hexagonal grid-like array has advantages that should be highlighted. The array fully covers the whole area of a surface. The distance between two central points of adjacent hexagons is always the same. In certain cases involving the investigation of the optical path from a point Ap to a point Bp, the calculation by the graphical method can be simplified by using the vectors situated within a limited angle, which reduces the number of trajectories to be investigated.

In the case of the hexagonal grid-like array, one can either divide each hexagon into six equilateral triangles, or create a first hexagonal grid-like array (with a size of 1 mm) and a finer hexagonal grid-like array (with a size of 10 microns) by utilising information obtained in the first phase in order to evaluate the second phase and to calculate the indices and the coefficients of attenuation of the second phase. The degree of definition of a medical scanner enables elements of about 1.5 mm$^3$ in size to be detected; in 1 mm$^3$ there are about 1 billion cells. It seems that a cancer develops in three phases: a slow phase, up to the time when the nodule reaches a critical size of about 50 microns, a vascularisation phase in which the cancer is connected to the organism by a blood network that develops in situ, and a more rapid phase in which the cancer becomes a true organ and invades the organism, where it discards waste material and possibly malignant cells.

Given these facts, a definition of 1 mm is insufficient to detect a cancer at the moment it starts to grow dangerously due to the vascularisation.

An improvement of the definition by a factor of 10 using conventional methods would involve an increase in the number of scannings by an X-ray beam and thus the irradiation by a factor of 1000, and would also increase the cost of the information processing by a factor of 1000.

A first object is to reduce the number of scannings and thus the level of irradiation. It is then necessary to find a method for processing the image more rapidly. Such a method may be based on a mathematical algorithm, the principle of which will be explained hereinafter.

It is thus necessary first of all to recall the principles of scanography and the current state of the art in this field. Scanography (or tomodensitometry) was discovered in 1968 by G. N. Hounsfield, an engineer working in the EMI company. The 1972 patent is entitled: "A method and apparatus for examination of a body by radiation such as X or gamma radiation". In 1979 the inventor was awarded the Nobel prize for his invention. The principle of the invention is as follows:

A beam of X-rays scans a defined plane, passes linearly through an organ, and strikes a plate or a radiographic detector. The passage through the organ produces an attenuation of the beam, the degree of attenuation being able to be measured by means of the detector. Crosswise scanning in the sectional plane produces a set of information that is processed by suitable software on an associated computer.

The information processing of a sufficient number of cross scannings, defining in fact small elementary cells or zones, enables a set of linear equations to be solved provided that the number of scannings is equal to the number of cells.

The editing and use of the information are carried out by an associated computer.

The computer collects the set of data and then calculates the value of the coefficient of attenuation of each elementary zone. The information obtained from these calculations is expressed by a map of the tomographic sectional plane.

The set of maps constitutes the three-dimensional scanner image of the analysis, which permits longitudinal or transverse sections. The medical interpretation is thus based on a real internal image of the tissues. The investigations are preceded or completed by other investigations, for example ultrasound echography or magnetic resonance imaging.

Scanning and the methods that it has introduced remain an essential tool of medical investigation. Nowadays volumes of each elementary zone of the order of mm$^3$ are obtained.

However, this is far from the microscopic scale since the number of living cells is of the order of 1 billion per mm$^3$. Human cells have on average a size of 10 μm. The microorganisms that are found in the human body may have a size of the order of 1 μm$^3$.

The early detection of cancer presupposes a considerable gain in definition. However, the length of time the system is used for a specific patient cannot exceed a certain economic threshold.

Thus, the combination of an accurate scanning apparatus together with masks of very small dimensions that can be positioned and switched in an extremely precise manner, and an information processing system providing an acceptable evaluation of the values of the coefficient of attenuation of each elementary micro-zone, enables the number of beam pulses and thus the number of profiles to be recorded to be reduced by a considerable factor, while at the same time increasing the definition from 1 mm to 10 or 20 microns without reaching a prohibitive level of irradiation.

To examine a 20×20 cm zone with a definition of 1 mm, as is currently carried out, the coefficients of attenuation relating to 200×200 points, i.e. 40 000 points, are obtained, which requires the production of 40 000 profiles. If it is desired to obtain a definition of 10 microns, it is necessary to have available values of the coefficients of attenuation of a number of points 10 000 times greater, i.e. 400 million points, and to subject the patient to a lethal level of irradiation, quite apart from the fact that this therefore involves delays and virtually prohibitive costs, regardless of whether the echograph or magnetic resonance imaging method is used.

In the process described here, it is necessary to produce 40 000 profiles in order to obtain a low definition image, followed by 40 000 supplementary profiles for the high definition crossed scanning, i.e. a total of 80 000 profiles instead of 400 million profiles, in other words a division by 5 000 in the number of profiles and associated irradiation.

However, the problem still remains of how to process the signal and the values associated therewith.

The inventor has thus been forced to perfect methods for processing the signal and associated information, so as to solve the particular problem concerning the evaluation of the terms of a rectangular matrix, representative of the sectional profiles of a specific area investigated by a scanner when approximate estimates relating to each term are available, but precise information is available concerning the sum of each line or column of the matrix.

Several methods have been perfected and investigated in order to solve the problem encountered in various imaging contexts. Research has led to an original method, which provides a considerable simplification in the calculation process with a view to obtaining the desired image, represented by a rectangular matrix.

In the case of medical imaging this enables the number of profiles to be produced to be reduced.

This method, which will now be described hereinafter, in fact enables matrices of larger size to be produced by a distribution or an extrapolation of the values of each term or zone of a low-definition initial matrix in order to obtain estimated values in micro-zones, obtained by slicing each term or zone of the initial matrix.

An expanded matrix is thus obtained.

This expanded matrix is then adjusted by a calculation process enabling each term to be reliably evaluated if it is desired to obtain the values of the boundary elements, a boundary element being the sum of the terms of a line or column.

In this case one may go for example from a 5×4 matrix containing 20 terms to a 25×20 matrix containing 500 terms, and then calculate each of the terms by the method described above.

This, then, involves expansion and adjustment of the initial matrix representative of the signals obtained, so as to obtain the various profiles.

The description of the adjustment method is described below. This method plays a special role in the calculation carried out after, where appropriate, obtaining a large dimension matrix from a smaller initial matrix.

The following description thus relates to the adjustment calculation method per se according to the invention. This method plays an important role in the processing of the signals obtained from the measurement, by the radiographic detectors, of the intensity or of the residual value of the primary beam produced by the X-ray apparatus, after the beam has passed through the organism being investigated.

If it is desired to process a matrix having dimensions of n lines and m columns, let Bij be the estimated value at the line i and at the column j, let Cij be the most probable value of the corresponding term of the matrix, let ρj be the sum of the terms of the column j, let cj be the sum of the terms of the line i.

The estimate of Bij is obtained either by the matrix expansion process, or by any other method providing such an estimate, in particular using linear or polynomial adjustment techniques.

In the present case the solution of the values of Cij will be sought, taking into account the constraints of lines and columns, that is to say the minimum of the following function is sought:

$\Sigma(Cij-Bij)^2$ for all values of i and j subject to the constraints:

$\Sigma Cij = \rho j$ for all the values of j $\Sigma Cij = ci$ for all the values of i The search for a minimum of the functions subject to constraints will be carried out using the method of Lagrange multipliers, the Lagrangian being written:

$$L = -\sum ij(Cij-Bij)^2 + \sum_{j=1}^{m} \lambda j \left( \sum_{i=1}^{n} (Cij-pj) \right) + \sum_{i=1}^{n} \mu i \left( \sum_{j=1}^{m} (Cij-ci) \right)$$

This function is composed of two parts, namely a first part that does not have a left-hand character, and a second part that is a set of linear relations.

The Lagrangian can thus be derived for the variables Cij and λj and μi, Lagrange multipliers associated with the line and column constraints (we have in fact two sets of constraints, namely the line constraints and the column constraints).

Under these conditions we are able to obtain a set of linear relations relating to the Cij by differentiating the Lagrangian, and a set of relation values relating to the constraint values, which is written:

By specifying that dL/dCij denotes a partial derivative of the function L for the variable Cij.

$$\frac{dL}{dCij} = -2(Cij-Bij) + \lambda j + \mu i = 0 \qquad 1$$

and the constraints $$\sum_{i=1}^{n} Cij = pj,$$

for all $j$

}2

$1 \Leftrightarrow Cij = Bij + (\lambda j + \mu i)/2$ $$\sum_{j=1}^{m} Cij = ci,$$

for all $i$

The set of n×m relations corresponding to the partial derivatives plus the n+m constraint relations is linear and allows only one solution corresponding to the nm+n+m variables.

If for example we wish to process a matrix where n, the number of lines, is equal to 25, and m, the number of columns, is equal to 30, then the solution by linear algebra consists in processing:

750 Cij variables 25 variables corresponding to the line multipliers, the $\mu i$ 30 variables corresponding to the column multipliers, the $\lambda j$.

A first objective is already achieved since only 55 profiles have to be obtained, instead of 750.

We have in total 750 relationships corresponding to the partial derivatives and 55 relationships corresponding to the constraints, for 805 variables. The solution of this problem by employing matrix calculus is the most obvious solution, but involves very tedious calculations, which are slightly more awkward than those involved in conventional methods. The aim of the inventor was first of all rapidly to improve the calculation processes, but over and above his essential objective, namely limiting the irradiation dose during an examination.

At this level one can operate a scanner that limits the level of irradiation but involves an extra cost on account of the calculations involved in the method that has just been described.

Although this method effectively permits a considerable limitation in the level of irradiation (or echography treatment), it involves a calculation process that is just as tedious as in the conventional methods for obtaining an estimate which, although generally satisfactory, nevertheless does not provide precise values of the coefficient of attenuation.

It was therefore necessary to continue investigating ways of trying to improve the calculation time.

Various algorithms have been used, which have provided some improvement, though the inventor has continued to try and find ways of improving significantly the calculation time.

The following is obtained by combining the aforementioned relationships:

$$\sum_{i=1}^{n} Bij + \frac{n}{2} * \lambda j + \left( \sum_{i=1}^{n} \mu i/2 \right) = pj$$

$$\sum_{i=1}^{m} Bij + \frac{m}{2} * \mu i + \left( \sum_{j=1}^{m} \lambda j/2 \right) = ci$$

One may deduce from these relationships:

$$\lambda j = \left(\frac{1}{n}\right) * \left( 2 * \left( pj - \sum_{i=1}^{n} Bij \right) - \sum_{i=1}^{n} \mu i \right)$$

$$\mu i = \left(\frac{1}{m}\right) * \left( 2 \left( ci - \sum_{j=1}^{m} Bij \right) - \sum_{j=1}^{m} \lambda j \right)$$

Under these conditions, by substituting for example the value of $\lambda j$ in $\mu i$, we obtain:

For all j $$\lambda j = \left(\frac{2}{n}\right) * \left( \left( pj - \sum_{i=1}^{n} Bij \right) - \sum_{i=1}^{n} \mu i \right)$$

For all i $$\mu i = \left(\frac{1}{n}\right)\left(\sum_{i=1}^{n} \mu i\right) + \left(\frac{2}{m}\right)\left( ci - \sum_{j=1}^{m} Bij - \left(\frac{1}{n}\right) * \sum_{j=1}^{m} \rho j + \sum ijBij * \left(\frac{1}{n}\right) \right)$$

If one defines that $\mu^- = (1/n)\Sigma(i=1 \text{ to } n) \mu i$ is the mean of the multipliers associated with the constraint of the lines, we arrive at the two following relationships:

for all j $$\lambda j = \left(\frac{2}{n}\right) * \left( \rho j - \sum_{i=1}^{n} Bi \right) - \mu^-$$

for all i $$\mu i = \mu^- + \left(\frac{2}{m}\right) * \left( ci - \sum_{j=1}^{m} Bij - \left(\frac{1}{n}\right) * \left( \sum_{j=1}^{m} \rho j - \sum ijBij \right) \right)$$

In fact:

$$\frac{1}{m}\sum_{1}^{m} * \sum_{1}^{n}$$

Under these conditions, and by substituting in the relationship:

$$Cij = Bij + (1/2) * (\lambda j + \mu i)$$

we arrive at the algebraic relationship.

This adjustment formula allows us to deduce the matrix of the Cij from the matrix of the Bij by term-by-term calculation $$Cij = Bij + \left(\frac{1}{n}\right) * \left( \rho j - \sum_{1}^{n} Bij \right) + \left(\frac{1}{m}\right) * \left( ci - \sum_{j=1}^{m} Bij \right) - \left(\frac{1}{nm}\right) * \left( \sum_{j=1}^{m} \rho j - \sum ijBij \right)$$

The inventor has thus succeeded in a totally surprising manner in carrying out an algebraic-type calculation that does not require the use of matrix calculus.

The algebraic method allows the partial treatment of the reference matrix, which in many cases may be sufficient.

The numerical validation of this method of processing signals and establishing definition values of the sought-after image in a medical context is described hereinafter.

Example of application of the method to a reduced model

Let us consider a matrix of n lines and m columns in which n=3, m=4

| INITIAL MATRIX | | | | | | |
|---|---|---|---|---|---|---|
| | 1 | 2 | 3 | 4 | Σ lines | C |
| 1 | 22 | 24 | 18 | 16 | 80 | 78 |
| 2 | 24 | 22 | 18 | 20 | 84 | 85 |
| 3 | 26 | 20 | 22 | 24 | 92 | 93 |
| Σ columns | 72 | 66 | 58 | 60 | 256 | |
| P | 70 | 67 | 59 | 60 | | 256 |

In this matrix the estimated values are entered in the three lines and in the four columns, and the line constraints are entered in the column C.

The column constraints are entered in the last line P.

The application of the above formula is simplified since the total of the column (or line) constraints is equal to the sum of the terms and leads to:

| EQUILIBRIUM AFTER CALCULATIONS | | | | | | | |
|---|---|---|---|---|---|---|---|
| | 1 | 2 | 3 | 4 | Σ 2 | C | Δ |
| 1 | 20.83333 | 23.83333 | 17.8333 | 15.5 | 78 | 78 | 0 |
| 2 | 23.5833 | 22.58333 | 18.5833 | 20.25 | 85 | 85 | 0 |
| 3 | 25.5833 | 20.5333 | 22.583 | 24.25 | 93 | 93 | 0 |
| Σ 2 | 70 | 67 | 59 | 60 | 256 | | |
| P | 70 | 67 | 59 | 60 | | | |
| Δ | 0 | 0 | 0 | 0 | | | |

It may be checked, by taking calculations performed on a simple calculator, that the value of the vertically or horizontally summated terms not only satisfies the constraints but also leads to the desired results. If one wished to use linear algebra to solve this problem, it would then be necessary to invert a matrix of size equal to n×m+n+m, i.e. in our case 19×19, the calculation time for which is obviously much too high.

The method that has been discovered permits a considerable reduction of the calculation time (of the same order of magnitude as the reduction in the level of irradiation).

By way of example, for a 200×200 matrix, which would require a treatment by linear algebra measurable in hours, the values of the 40 000 terms, their representation in the form of colours and the construction of iso-attenuation lines are obtained in less than two seconds.

As has been explained above, the use of any other optical system in the field of frequencies where wavelengths are close to the visible or infra-red range, raises the problem of the refraction of the light rays. The apparatus according to the invention solves this problem.

The two following methods may then be combined:
  in the method for calculating the optical path, for multiple scannings, the optical path between for example a point A and a plurality of points B1, B2, B3, etc. is then obtained, and an equation connecting the refractive indices of the traversed media corresponds to each optical path. If the number of scannings is sufficient a precise evaluation of the refractive indices of each mini-zone within the object examined by tomodensitometry will be obtained.
  the matrix expansion and adjustment method as used for the X-ray scanner will enable the resolution of the system to be improved so as to obtain a suitable value of the "elementary" refractive indices of each micro-zone resulting from the distribution of the mini-zones by the matrix expansion process. A high-definition image is then obtained giving refractive indices of each micro-zone and the corresponding coefficients of absorption or attenuation. In fact, once the refractive indices are known at all points the residual luminous intensity at the end of each trajectory will be measured and the positions of the singularities will be found by the methods described hereinbefore, similar to those used for the X-ray scanner, so as to obtain not only an image of the refractive indices but also an image of the coefficients of attenuation.

A reading of this image can provide the operator with information on the singularities found in the interior of the examined object, either by a two-dimensional examination or by a three-dimensional examination by successively processing a plurality of densitometric planes.

Two embodiments of an apparatus according to the invention are described hereinafter. Two systems are envisaged, differing basically in the mode of displacement of the laser beam in a tomographic plane. In both cases a YAG NEODYNE laser of 1.064 microns wavelength or a YLF laser of 1.110 microns wavelength will preferably be used. The energy per pulse is between 5 and 10 millijoules. The size of the beam can be altered by the optical system, and can vary between 1 and 5 microns. The pulse duration is between 1 and 5 nanoseconds. The duration will depend in particular on the reaction time of the photoelectric cells of the reader. If the reaction time of the photoelectric cells is of the order of a microsecond, pulse times of the same order of magnitude must be used and the energy of the beam must consequently be adjusted. The laser may weigh several kilograms.

One may also use a fibre-optic system displaceable in the vicinity of the object to be examined and carried by an orientatable rod that is self-displaceable on a ramp. For fine exploratory work a two-dimensional fibre-optics beam will be used, the beam itself being displaceable and orientatable.

A first system envisages that for each plane the beam has a fixed position and the displacement of the beam is effected by means of a mirror displaceable on a ramp and orientatable by rotation at each point of its position on the ramp. A second system envisages that the laser is displaced on the ramp and is orientatable by rotation at each point on the ramp.

A view of the first system is shown in FIG. 3. In this FIG. 30 denotes a floor, 31 an adjustment means for the supporting feet of the table, 32 supporting cylinders, 33 sliding tubes, 35 Teflon toruses that enable the vibrations to be filtered out, 34 a supporting plate made of non-deformable material, of rigid metal, granite or marble, so as to filter out or dampen any residual vibration, 36 a means for fixing the laser on the plate, 37 a laser tube, 38 an orientatable mirror, 39 a means for fixing the bracket to the support, 41 a detection plate consisting of photoelectric cells, 42 a horizontal rail of the bracket, 40 a plate to protect the cells against over-exposure, 43 a supporting rod for the mirror, 44 an object to be examined, 45 or 46 an incident laser ray, 45' or 46' a parallel laser ray, 47 a rotatable, displaceable supporting plate for the object to be examined and also transparent to infra-red radiation, and 48 denotes a bracket.

The operation of this system is as follows. The supporting plate 47 is placed at the desired height by moving, within the supporting cylinder 32, the sliding tube 33 and a small plate for supporting torus-shaped joints 35. The sliding tube 33 has no contact with the supporting cylinder 32 other than through the Teflon torus-shaped joint 35, which filters practically all vibrations. The supporting rod 43 for the mirror 38 is displaced to the required position, and the mirror 38 and the laser 37 are orientated so that the incident laser ray 45 is orientated as desired.

Different scanning programs enable profiles p to be obtained at a low definition, or by k*p=X+Y shots in two crossed series for a high definition. In the first case the elementary surface of each cell or micro-elementary grade unit is of the order of 1 mm$^2$. In the second case the size of the elementary cell may be of the order of 100 microns and may be as small as 1 micron (practical limit taking into account the wavelength).

In order to obtain the desired definition, the beam is passed through an optics system integrated in the laser tube, enabling its diameter at the level of the object to be examined to be increased up to 1 mm or to be reduced to 1 micron.

In the case of small diameters two procedures may be adopted, jointly or otherwise, by implementing the operation so that the duration of a pulse is reduced in order to decrease the thermal effects on the objects to be traversed or on the photoelectric cells of the detection means, or by inserting a device 40 for absorbing the infra-red energy. The implementation of a tomographic plane will thus be effected as follows:

In a first stage the beam will be regulated and the detection plate will be adjusted so as to function for example at a definition of 1 mm, and a scanning program will be defined so as to obtain a number of profiles equal to the surface in mm$^2$ of the section of the object, and the scanning program will be executed by transferring the results obtained from the cells to the computer.

In a second stage, the beam and the detection plate will be regulated so as to obtain the desired high definition, and a crossed scanning program will be established depending on the zone to be explored in the cross-section of the object, on the angle (generally a right-angle) between two parallel high definition scannings or non-high definition scannings, and on the opacity of the object, so as to regulate the duration of the pulses and the possible absorption.

The data obtained at the cellular level will be transferred to the computer, which will carry out the data processing and store the results.

In a third stage, the results of the calculation will be used to produce an image of each tomographic plane by means of a printer using or not scales of greyness or colours.

The use of the previously described algorithm will take place under identical conditions. The process thus used permits a very considerable saving in calculation time in proportions identical to those obtained for the X-ray scanner.

In the chosen mode of operation the mirror 38 pivots about an axis of rotation, in the same way as the laser beam, so as to obtain parallel traversing rays 46 and 46'. The mirror will be able to be moved a sufficient distance so as to obtain two series X and Y of profiles k*p such that in each series the traversing rays are parallel to one another and that the two series intersect.

The volume of a singularity C will be able to be obtained by simply counting in a given plane the small squares having a certain level of colouration, and then adding the numbers obtained in the adjacent planes and for adjacent zones, between two limiting planes defined by observation.

The database consisting of the set of results relating to the different planes will be able to reveal the black zones resulting from the absolute opacity of certain inclusions, which would prevent certain zones thus hidden from being seen.

In order to illuminate this zone two ways at least can be adopted, namely either to turn the object to be examined so as to obtain a plurality of images at different angles after having placed in position microscopic reference elements so as to reconstitute a complete image, or to turn the bracket 48 so as to obtain images of hidden zones.

In both cases the object to be examined should be placed on and if necessary fixed to the transparent plate 47, which is capable of turning about an axis.

In this first system reflection by the mirror becomes difficult for certain wavelengths, resulting in losses of light energy that may vary with the angle of reflection, which can complicate the calculation by requiring that more complex reference measurements be made in the absence of the object.

On the other hand, the rotation and the translation of the mirror 38 is greatly facilitated by its low weight, and only requires low power piezoelectric actuators.

Figure 4:
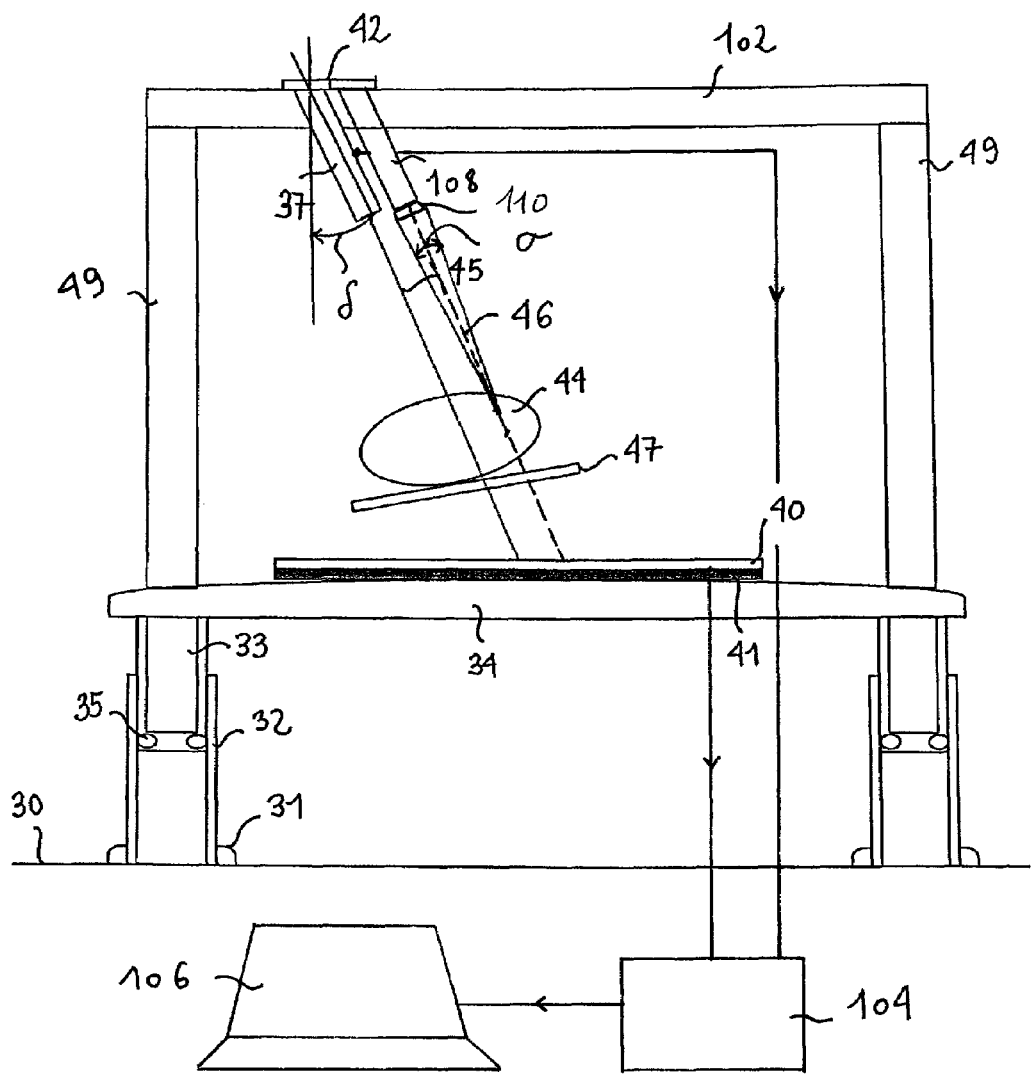
FIG. 4 is a plan view of an apparatus according to a second embodiment of the invention.

A view of the second system is shown in FIG. 4, in which identical reference numerals denote identical elements. The reference numeral 49 denotes a frame.

The functioning of the system is as follows.

The supporting plate 34 is placed at the desired height by moving within the interior of the supporting cylinder 32 the sliding tube 33 and a small supporting plate for torus-shaped joints 35. The plate 47 for supporting the object to be examined is positioned at the chosen angle. The same procedure as for the first system is then followed. In order to illustrate the scannings reference will be made to FIG. 18, which shows the displacement of the beam 37 at a distance from a first position and the choice of a new inclination of the beam 37 so as to obtain two intersecting scannings. The beams 45 and 45' are parallel to one another in each of the scannings.

In this second system the translation and the rotation of the laser beam 37 require more powerful actuators. In this case too the use of the previously described algorithm will provide the same advantage. The process that is thus used will permit a very considerable saving in calculation time of the same scale as that obtained for an X-ray scanner.

It may be noted that the attenuation may, in the case of infra-red radiation, be the result of several phenomena, such as reflection inside the object, a refraction in specific zones, and absorption of the infra-red energy converted into heat.

It will therefore be important to measure also the rise in temperature, where this is possible, in different zones, so as to distinguish the various sources of attenuation.

The nature of the object is then important, and the possibility of being able to turn the object for different measurements enables useful information to be obtained in the evaluation of errors resulting from reflection or refraction, which depend on the wavelength and the corresponding refractive index for the different materials.

In order to avoid reflection phenomena it is possible to produce a thin layer of material of low refractive index by vapour phase deposition on a very thin film of plastics material and to envelope the organism with this film 50.

Figure 5:
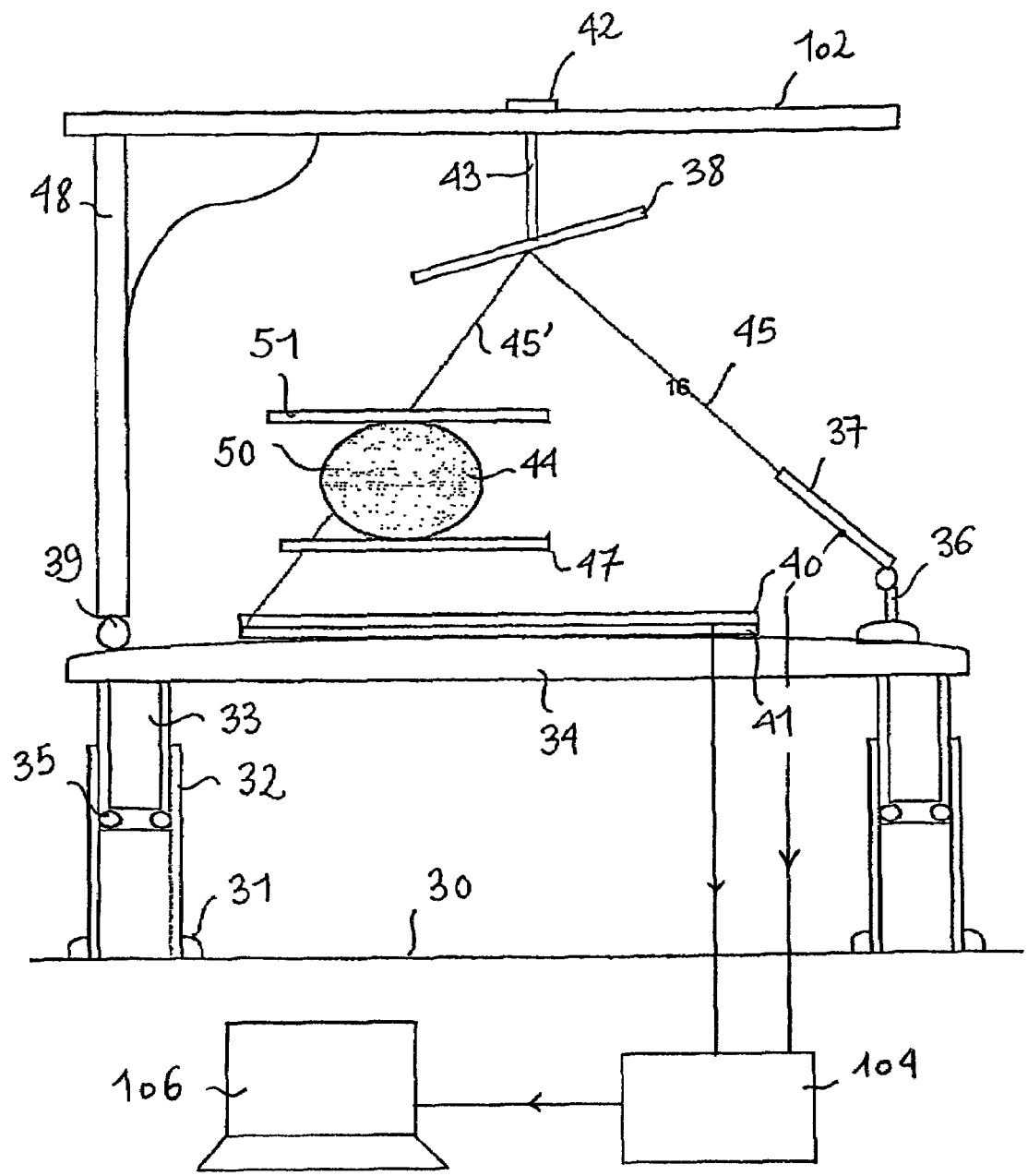
FIG. 5 is a plan view of an apparatus similar to that of FIG. 3.

As regards refraction, in the case where a laser is used, that is to say coherent light is produced, the phenomenon may be different to when a non-coherent light is used, though there still exists a certain degree of refraction that can be decreased, FIG. 5, by arranging the organism or object 44 between two transparent plates 47 and 51, one of the plates forming the support plate described in the examples illustrated in FIGS. 25 and 26, coated with anti-reflecting layers so as to avoid reflection, and which are also strictly parallel so as to limit the refraction that they may cause.

Thus, the combination of the two systems, namely X-ray scanner of infra-red laser scanner, leads to an improvement of the image quality and of its definitions.

However, in the two infra-red scanner systems described here, the method according to the invention allows the number of profiles obtained by infra-red laser to be reduced to such an extent for high definitions that the rise in temperature will still be controllable, thereby avoiding an excessive heating of the investigated object or organism, or if the traversed body comprises zones whose refractive indices are similar.

As has already been explained, the calculation times will remain within the limits of the normal methods for processing the information.

The first application is for therapeutic use. In fact, a cancerous nodule or a group of cells can be destroyed by focusing a very high energy infra-red laser beam, but operating for a very short time, in order to destroy a target as a result of the rise in temperature of the zone situated around the focal point.

Such procedures are used in particular in ophthalmology. The method may be extended to other parts of the body if a preliminary investigation can be carried out by the described methods so as to obtain a true map of the refractive index and coefficients of absorption of a specific wavelength. One will thus be able to simulate on a screen the optical path in different positions of inclination of the beam and to target precisely the nodule or group of cells to be reached, while evaluating by means of the coefficients of absorption the energy to be directed onto the target.

In fact, the scanning and adjustment of a plane situated in an object leads to a precise evaluation of the indices of refraction and the coefficients of absorption at any point in the examined space.

If this investigation provides evidence of a singularity such as a blood clot (in particular cerebral clot), tumour (malignant or otherwise), it is possible to act quickly so as to destroy the said singularity.

In order to achieve such a result a suitable apparatus must be employed. As illustrated in FIG. 4, this apparatus comprises a bracket on which are fixed an exploratory laser and a treatment laser, these two lasers being able to move along the bracket and to be inclined so as to scan the space below the lasers. The two lasers preferably operate at the same wavelength, for example in the infra-red range at 1.064 microns, although their functioning and role are very different. A detector enables the residual luminous intensity to be measured after passage of the beam through the object and its transparent support, as well as the deviation caused by the passage of the beam through the object. This detector will basically be used in the exploratory phase, and can be shielded so as not to be affected by the treatment laser, the power of which may be very much greater.

The exploratory laser will be used to determine the refractive indices at all points of the object, as has been explained hereinbefore.

The treatment laser will be used to focus the high energy of the treatment laser on the singularity. This treatment laser is therefore provided with an optics system enabling the beam to be focussed.

The operation is thus carried out in two stages

In a first stage the exploratory laser enables the refractive index to be calculated at all points of the section in question, and thus to determine the position of the singularity which, on account of the two sets of information that it provides, namely relating to anomalies of the refractive indices and anomalies of the coefficients of attenuation (or absorption), will facilitate the identification of the singularity and enable its position to be located precisely.

In a second stage the treatment laser will be used in a repetitive manner by focussing the beam on the singularity to be destroyed. In order to achieve this focussing, it will be necessary to calculate the optical paths from the various ends of the beam up to the singularity and to adjust, by means of an optical focussing system, for example a displaceable lens 110, the focal point of the beam so that it is located in the zone of the singularity. All the calculations of the various optical paths can be performed since the different refractive indices are known. This prior knowledge of the optical paths enables the optical focussing system to be targeted on the singularity.

Wavelengths other than the infra-red wavelengths will also be able to be used, depending on the medium to be treated or traversed. It is even possible to use a laser provided with a frequency multiplication system, as has been suggested by Danièle ARON ROSA and Michèle GRIESEMANN in U.S. Pat. No. 4,309,998 entitled "Process and apparatus for ophthalmic surgery".

In fact, the extreme optical paths would lead in the absence of the object to a virtual focal point. The interposition of the object displaces the focal point so that it coincides with the zone where the tumour or the singularity is located. In a large number of cases where the beam and the focussing lens are coaxial, it must be checked that the virtual optical paths are symmetrical with respect to the axis of the beam. If this is not the case, a translation or a rotation of the laser must be simulated so that this coaxiality condition is checked before operating the laser.

In the case of the treatment laser, an apparatus comprising a very high energy laser operating for a very short period, for example 100 femtoseconds, i.e. $500 \times 10^{-15}$, will preferably be used. If the energy that is to be concentrated is equal to 1 joule, the power of the laser is then measured in terawatts. If one wishes to avoid causing damage in zones close to the singularity, it is preferable to repeat the shots, for example 1500 times in 100 milliseconds, and to displace the beam for example by 100 steps, i.e. one step per millisecond, by moving a distance of 10 to 100 microns each time.

This assumes that the bracket can allow extremely rapid step by step displacements of very low amplitude, and that the laser can be switched (pulsed) several thousand times a second. A very high increase in temperature will thus be able to be produced in a small size of 10 to 100 microns, without causing heating that would damage the tissues or surrounding environment of this zone.

The application to a medical infra-red laser scanner is only one of the possible applications of the calculation of the optical path, which may be complemented if desired by simultaneously measuring the point indices or refraction and/or the point coefficients of attenuation.

A second application relates to the detection of objects situated in an aqueous medium. In fact, certain wavelengths around 1.06 microns may be used, which are only slightly absorbed by water, to detect or describe objects such as aquatic animals, divers, or any other underwater objects. In addition, in some cases it will be necessary to use high-energy (measured in terawatts) infra-red lasers for very short times measured in femtoseconds.

In the case of searching for persons in a lake, a swimming pool or any other surface containing water, the following procedure will be able to be adopted:

Perform an infra-red laser scanning by reflecting the beam to a detector, and installing a detector at a certain depth, or by using the reflection by the object itself.

Once the object has been detected a single infra-red camera can be trained on the spot in order to check the nature of the object or to carry out a scanning operation of the examined space by a series of scannings as described above.

More generally, if for example an infra-red camera or photographic apparatus is used, the image can be rectified and improved if the optical path from the apparatus to the object is known, so as to take into account deformations and deviations produced by the changes in refractive indices in the medium.

The detection of an object in an aqueous medium by sonar equipment raises the problem of the velocity of propagation of the sound wave, which in water is about 200 000 slower than a light wave or, more generally, an electromagnetic wave.

An object moving rapidly, for example 30 meters a second at a depth of 100 meters, will move 6 meters during the outward and return path of the sound wave, and only a few tenths of a micron if an electromagnetic wave is used.

Another application relates to aerial detection. In fact, the scanning of an air space by an infra-red laser not only has obvious advantages compared to acoustic methods of detection, but also compared to Hertzian waves, on account of the fineness of the beam, which permits a better definition of the image and facilitates the use of an imaging method of the type described in the aforementioned patents and thus facilitates the investigation and identification of shapes.

Alarm systems will also benefit from the techniques described here, by enabling any unusual object to be detected.

The method of investigating the optical path may be applied by carrying out certain adjustments to the investigation of the path of a sound wave or indeed ultrasound wave, with which it may be combined, in particular in the field of cancer treatment using ultrasound waves converging on the cancerous nodule that it is desired to destroy by heating, in which connection the propagation of sound waves may be analysed by using Euler's equations, which lend themselves to various processes enabling the numerical calculation of the propagation of a sound wave. A method similar to that described by the inventor relating to the optical path would also enable the sound path in a heterogeneous medium to be plotted so as to simplify the technical and therapeutic procedure.

More generally, in particular in oil exploration work, an analysis of the soil strata would greatly benefit investigations as regards the optical path or acoustic path.

Thus, the optical path calculation method, by establishing curves of possible paths between two points and thereby enabling the minimum optical path between two points to be determined, allows several technical operations to be carried out:

tracing in a medium in which the refractive indices of each zone are known, so as to obtain the coefficients of absorption at all points and thereby identify singularities.

calculation of the refractive indices at all points using even imperfect estimates of these indices obtained by a knowledge of the medium provided by an X-ray scanner, by performing a series of laser scannings covering the investigated surface and repeating these scannings if necessary.

forming high-definition optical images by applying the expansion and adjustment methods described hereinbefore, thereby facilitating the use of infra-red laser scanners.

use of the method for the rapid detection of anomalies or objects specifically in a liquid or gaseous medium.

in therapeutic use, this method will allow a precise course of action in order to destroy cells or groups of malignant or benign cells, enabling the optical path of a laser beam, for example infra-red laser beam, to be determined and focussed on the target forming the zone to be destroyed.

Given the similarity of the laws of propagation of sound and the laws of propagation of light, the method may be extended, taking all the necessary precautions in use, to the plotting of the acoustic path in a heterogeneous medium. Under these conditions the destruction of these cells may be carried out also after targeting, by focussing on the zone to be treated a high energy ultrasound beam capable of producing a heating effect so as to destroy the targeted cells.

Provided that the necessary precautions are always adopted, the technique of tracing the acoustic path by a method similar to that described in this patent may also facilitate oil prospecting by the analysis of soil strata, in particular by seismic refraction.

The invention claimed is:

1. Apparatus for determining a refractive index in a large number of points p, of a physical medium, each point being defined by a fixed reference point occupying the centre of gravity of an elementary grid unit or block, in which p elementary grid units form a grid-like array of the physical medium, wherein the apparatus comprises:

a light laser, preferably an infra-red laser, displaceable in elementary steps along a displacement guide or fixed with respect to a mirror displaceable in elementary steps along the displacement guide, in order to carry out a series of p coplanar pulsed laser rays each starting from a starting point Ap defined with respect to the displacement guide and arriving at an arrival point Bp defined by a detection means, after having passed through the physical medium along an optical path defined as being the shortest optical trajectory between the two points Ap and Bp;

a counter time-synchronised with each pulsed laser ray so as to record an instant Tp when each pulsed laser ray reaches the arrival point Bp counting from the initial instant when the pulsed laser ray has left the starting point Ap; and a computer programmed to carry out the following steps:

(1) to investigate the optical path from among the optical trajectories all leaving from the starting point Ap and all arriving at the arrival point Bp, each optical trajectory being defined by a sequence of elementary optical paths (L), each equal to the arithmetic product of two terms, in which the first term is a modulus of a vector connecting two centres of gravity of two adjacent elementary grid units, and in which the second term is an estimated refractive index at each centre of gravity;

(2) starting from p linear equations connecting, for each of the p investigated optical paths, the elementary optical paths (L) and the indices of refraction (N) to the detected passage time Tp, to construct a square matrix of the elementary optical paths [L], a vector of the refractive indices of the elementary grid units [N] and a vector of the passage times of the light ray [T] and to solve the matrix equation;

$$[N]*[L]=[T]$$

with respect to the vector of the refractive indices of the elementary grid units [N]; and (3) to repeat the steps (1) and (2) so as to investigate new optical paths with the refractive indices of the elementary grid units calculated during an immediately preceding iteration, to solve the matrix equation with the new elementary optical paths corresponding to the new investigated optical paths, and obtain a new vector of the refractive indices of the elementary grid units until the matrix of the elementary optical paths [L] converges and the vector of the refractive indices of the elementary grid units [N] also converges.

2. Apparatus according to claim 1, wherein in order to determine a coefficient of attenuation at any point of the physical medium where a refractive index has been determined:

the detection means is adapted so as to detect a variation of intensity ($\Delta$lp) of each pulsed laser ray of the series between the starting point Ap and the arrival point Bp taking into consideration an attenuation of the light intensity along the elementary optical paths followed by each pulsed laser ray, which is a function of a coefficient of attenuation E associated with each elementary grid unit; and the computer is programmed so as to carry out the following supplementary step:

(4) starting from p linear equations connecting the elementary optical paths (L) for which the vector of the refractive indices of the elementary grid units has converged in stage (3) and the coefficients of attenuation (E) of the elementary grid units to the variation in intensity ($\Delta$lp) of each of the p pulsed laser rays of the series, to construct a vector of the coefficients of attenuation of the elementary grid units [E] and a vector of the variations of intensity ($\Delta$lp), and then by a mathematical method involving linear algebra to solve the matrix equation:

[E]*[L]=[$\Delta$lp]

with respect to the vector of the coefficients of attenuation of the elementary grid units [E].

3. Apparatus according to claim 1, wherein the computer carries out stage (1) by being programmed to investigate the optical path by a method involving the calculation of a minimal critical path from estimates of the refractive indices obtained by an imaging method using an X-ray scanner, a nuclear magnetic resonance imaging unit, or an echography unit.

4. Apparatus according to claim 1, wherein in order to arrive at an estimate of the refractive indices with a greater spatial resolution with respect to the physical medium:

the displacement guide is provided with a micro-actuator displacing the light laser or the mirror along the displacement guide by an elementary micro-step equal to the elementary step divided by an amplification factor K so as to carry out two crossed series of pulsed laser rays X and Y respectively, both coplanar and each starting from a starting point Ax or Ay defined with respect to the displacement guide and arriving at an arrival point Bx or By defined by the detection means after having passed through the physical medium along an optical path defined as being the shortest optical trajectory between the two points Ax and Bx or Ay and By, and the computer is programmed to carry out the following supplementary stages:

(5) to investigate the optical path among a large number of optical trajectories all starting from the starting point Ax or Ay and all arriving at the arrival point Bx or By, being defined by a sequence of micro-elementary optical paths ($\mu$L) each equal to the arithmetic product of two terms, in which the first term is a modulus of a vector connecting two centres of gravity of two adjacent elementary micro-grid units and in which the second term is a refractive index (N') at each centre of gravity of each elementary micro-grid unit equal to the refractive index of the elementary grid unit from which the elementary micro-grid units are derived after division by the expansion factor K and for which the vector of the refractive indices of the elementary grid units [N] has converged in (3), and from K*p=X+Y linear equations connecting, for each of the investigated optical paths of one series X and the other series Y of the two series of pulsed laser rays, the micro-elementary optical paths ($\mu$L) and the refractive indices of the elementary micro-grid units (N') to the passage time Tx or Ty detected by means of the counter time-synchronised with each pulsed laser ray reaching the arrival point Bx or By starting from the initial instant when the pulsed laser ray left the starting point Ax or Ay, to construct a square matrix of the micro-elementary optical paths ($\mu$L), a vector of the refractive indices of the elementary micro-grid units [N'] and a vector [T] of the passage times of the light ray, and then (6) to adjust the refractive index in each elementary micro-grid unit by a method of least squares taking into account constraints imposed by the boundary values that formed by the detected passage times Tx or Ty, using the following formula:

$$Cij = Bij + \left(\frac{1}{n}\right)*\left(\rho j - \sum_{1}^{n} Bij\right) + \left(\frac{1}{m}\right)*\left(ci - \sum_{j=1}^{m} Bij\right) - \left(\frac{1}{nm}\right)*\left(\sum_{j=1}^{m} \rho j - \sum ijBij\right)$$

where, in this formula,

Cij is the sought value

Bij is the initially estimated value (n) is the number of lines of a representative matrix of a table of the refractive indices of the micro-elementary grid units (m) is the number of columns of a representative matrix of a table of the refractive indices of the micro-elementary grid units $$\sum_{i=1}^{n} Cij = pj$$

for all the values of i, the constraint of the column j $$\sum_{j=1}^{m} Cij = ci$$

for all the values of j, the constraint of the line i.

5. Apparatus according to claim 4, wherein in order to arrive at an estimate of the coefficients of attenuation with a greater spatial resolution with respect to the physical medium:

the computer is programmed to carry out the following supplementary step:

(7) starting from a variation of intensity ($\Delta$lx, $\Delta$ly) detected by the detection means for each pulsed laser ray of the two crossed series of pulsed laser rays X and Y between the starting point Ax or Ay and the arrival point Bx or By and taking into consideration an attenuation of luminous intensity along the micro-elementary optical path followed by each pulsed laser ray, which is a function of a coefficient of attenuation (E') affecting each elementary micro-grid unit and equal to the coefficient of attenuation (E) of the elementary grid unit from which the elementary micro-grid units are derived, divided by the expansion factor K, and from K*p=X+Y linear equations connecting, for each of the investigated optical paths of one series X and the other series Y of the two series of pulsed laser rays, the micro-elementary optical paths (μL) and the coefficients of attenuation of the elementary micro-grid units (E') to the variations of luminous intensity (Δlx, Δly), to construct a square matrix of the micro-elementary optical paths (μL), a vector of the coefficients of attenuation of the elementary micro-grid units [μE'] and a vector (Δl) of the variations in luminous intensity; and (8) to adjust the coefficients of attenuation in each elementary micro-grid unit by a method of least squares, taking into account constraints imposed by the boundary values that form the detected variations in luminous intensity Δlx or Δly, using the following formula:

$$Cij = Bij + \left(\frac{1}{n}\right) * \left(pj - \sum_{1}^{n} Bij\right) +$$

$$\left(\frac{1}{m}\right) * \left(ci - \sum_{j=1}^{m} Bij\right) - \left(\frac{1}{nm}\right) * \left(\sum_{j=1}^{m} \rho j - \sum ijBij\right)$$

where, in this formula,

Cij is the sought value

Bij is the initially estimated value (n) is the number of lines of a representative matrix of a table of the refractive indices of the micro-elementary grid units (m) is the number of columns of a representative matrix of a table of the refractive indices of the micro-elementary grid units $$\sum_{i=1}^{n} Cij = pj$$

for all the values of i, the constraint of the column j $$\sum_{j=1}^{m} Cij = ci$$

for all the values of j, the constraint of the line i.

6. Apparatus according to claim 1, wherein in the case where the physical medium is a part of a human or animal body and in order to treat a singularity of the refractive indices representative of a tumour or another pathological condition of a part of this body, it comprises a treatment light laser pulsed so as to generate a beam of very short duration, preferably 100 femtoseconds, and with a very high energy, mounted on the displacement guide and provided with a displaceable lens so as to adjust a focal length along a neutral axis of the lens and to cause the beam to converge at the focal point of the neutral axis; and the computer is programmed to carry out the following supplementary steps:

(9) to search for a singularity C among the refractive indices calculated on completion of step (3) or adjusted on completion of step (6) or among the coefficients of attenuation calculated on completion of step (4) or adjusted on completion of step (8), and to define by referencing the grid units or the elementary micro-grid units of the singularity C with respect to the displacement guide, and

(10) to investigate, for a plurality of points of the lens, the optical path between a starting point Aq and the singularity C regarded as the point of arrival, and to calculate a mean angle of convergence (σ) on the various investigated optical paths starting from different points of the lens and obeying a symmetry condition with respect to the beam, so as to adjust the focal length at a virtual focal point determined by the angle of convergence assuming that the beam travels in air, in such a way as to focus the said beam on the virtual focal point so that the singularity C coincides with a real focal point that can be destroyed, preferably by vaporisation, under the action of repeated pulses of the light laser.

7. Apparatus according to claim 1, wherein the light laser pivots about an axis that itself moves linearly by means of a stepping motor or by means of piezoelectric actuators.

8. Apparatus according to claim 1, wherein it comprises multiple detection bars for producing simultaneously a plurality of parallel images capable of being processed individually or in three dimensions.

9. Apparatus according to claim 1, wherein it comprises supports for a light laser, in particular an infra-red light laser or ultrasound laser, on which the stepping motors or the piezoelectric actuators enable a light beam to be oriented (α,β) or to be displaced.

10. Apparatus according to claim 1, wherein a mirror is displaced by a stepping motor or by a micro-actuator along the displacement guide and is displaced by rotation about a pivotal point by means of piezoelectric actuators, in order to reflect an infra-red laser beam so as to effect the p coplanar pulsed laser rays or the k*p=X+Y pulsed laser rays of the crossed series, the infra-red rays in each case being mutually parallel and intersecting both a series X and a series Y.

11. Apparatus according to claim 1, wherein it comprises two transparent plates coated with anti-reflecting layers in order to prevent a reflection of the infra-red beam formed by the pulsed laser rays, and which are parallel in order to limit a refraction of this beam, the object to be examined being arranged between the two plates and resting against one of them serving as support plate.

12. Computer program to be loaded in a computer used in an apparatus according to claim 1 to perform the following steps:

(1) to investigate by a method involving the calculation of a minimal critical path from estimates of refractive indices, the optical path from among the optical trajectories of a series of p pulsed laser rays all leaving from a starting point Ap and all arriving at a arrival point Bp, each optical trajectory being defined by a sequence of elementary optical paths (L), each equal to the arithmetic product of two terms, in which the first term is a modulus of a vector connecting two centres of gravity of two adjacent elementary grid units, and in which the second term is an estimated refractive index at each centre of gravity;

(2) starting from p linear equations connecting, for each of the p investigated optical paths, the elementary optical paths (L) and the indices of refraction (N) to a passage time Tp for each pulsed laser ray to reach the arrival point Bp starting from the starting point Ap, to construct a square matrix of the elementary optical paths [L], a vector of the refractive indices of the elementary grid units [N] and a vector of the passage times of the light rays [T] and to solve the matrix equation;

[N]*[L]=[T]

with respect to the vector of the refractive indices of the elementary grid units [N]; and (3) to repeat the steps (1) and (2) so as to investigate new optical paths with the refractive indices of the elementary grid units calculated during an immediately preceding iteration, to solve the matrix equation with the new elementary optical paths corresponding to the new investigated optical paths, and obtain a new vector of the refractive indices of the elementary grid units until the matrix of the elementary optical paths [L] converges and the vector of the refractive indices of the elementary grid units [N] also converges.

13. Computer program according to claim 12, wherein the following supplementary stage is carried out:

(4) starting from p linear equations connecting the elementary optical paths (L) for which the vector of the refractive indices of the elementary grid units has converged in stage (3) and the coefficients of attenuation (E) of the elementary grid units to a variation in intensity (Δlp) of each of the p pulsed laser rays of the series, to construct a vector of the coefficients of attenuation of the elementary grid units [E] and a vector of the variations of intensity [Δlp], and then by a mathematical method involving linear algebra to solve the matrix equation:

[E]*[L]=[Δlp]

with respect to the vector of the coefficients of attenuation of the elementary grid units [E].

14. Computer program according to claim 13, wherein the following supplementary stages are carried out:

(5) to investigate the optical path among a large number of optical trajectories of two crossed series of pulsed laser rays X and Y all starting from a starting point Ax or Ay and all arriving at a arrival point Bx or By, being defined by a sequence of micro-elementary optical paths (μL) each equal to the arithmetic product of two terms, in which the first term is a modulus of a vector connecting two centres of gravity of two adjacent elementary micro-grid units and in which the second term is a refractive index (N') at each centre of gravity of each elementary micro-grid unit equal to the refractive index of the elementary grid unit from which the elementary micro-grid units are derived after division by the expansion factor K and for which the vector of the refractive indices of the elementary grid units [N] has converged in (3), and from K*p=X+Y linear equations connecting, for each of the investigated optical paths of one series X and the other series Y of the two series of pulsed laser rays, the micro-elementary optical paths (μL) and the refractive indices of the elementary micro-grid units (N') to a passage time Tx or Ty for each pulsed laser ray to reach the arrival point Bx or By starting from the starting point Ax or Ay, to construct a square matrix of the micro-elementary optical paths [μL], a vector of the refractive indices of the elementary micro-grid units [N'] and a vector [T] of the passage times of the light ray, and then (6) to adjust the refractive index in each elementary micro-grid unit by a method of least squares taking into account constraints imposed by the boundary values that formed by the passage times Tx or Ty, using the following formula:

$$Cij = Bij + \left(\frac{1}{n}\right) * \left(\rho j - \sum_{1}^{n} Bij\right) + \left(\frac{1}{m}\right) * \left(ci - \sum_{j=1}^{m} Bij\right) - \left(\frac{1}{nm}\right) * \left(\sum_{j=1}^{m} \rho j - \sum ijBij\right)$$

where, in this formula,

Cij is the sought value

Bij is the initially estimated value (n) is the number of lines of a representative matrix of a table of the refractive indices of the micro-elementary grid units (m) is the number of columns of a representative matrix of a table of the refractive indices of the micro-elementary grid units $$\sum_{i=1}^{n} Cij = \rho j$$

or all the values of i, the constraint of the column j $$\sum_{j=1}^{m} Cij = ci$$

for all the values of j, the constraint of the line i.

15. Computer program according to claim 14, wherein the following supplementary stages are carried out:

(7) starting from a variation of intensity (Δlx, Δly) for each pulsed laser ray of the two crossed series of pulsed laser rays X and Y between the starting point Ax or Ay and the arrival point Bx or By and taking into consideration an attenuation of luminous intensity along the micro-elementary optical path followed by each pulsed laser ray, which is a function of a coefficient of attenuation (E') affecting each elementary micro-grid unit and equal to the coefficient of attenuation (E) of the elementary grid unit from which the elementary micro-grid units are derived, divided by the expansion factor K, and from K*p=X+Y linear equations connecting, for each of the investigated optical paths of one series X and the other series Y of the two series of the pulsed laser rays, the micro-elementary optical paths (μL) and the coefficients of attenuation of the elementary micro-grid units (E') to the variations of luminous intensity (Δlx, Δly), to construct a square matrix of the micro-elementary optical paths [μL], a vector of the coefficients of attenuation of the elementary micro-grid units [μE'] and a vector [Δl] of the variations in luminous intensity; and (8) to adjust the coefficients of attenuation in each elementary micro-grid unit by a method of least squares, taking into account constraints imposed by the boundary values that form the detected variations in luminous intensity Δlx or Δly, using the following formula:

$$Cij = Bij + \left(\frac{1}{n}\right) * \left(\rho j - \sum_{1}^{n} Bij\right) +$$

-continued $$\left(\frac{1}{m}\right)*\left(ci - \sum_{j=1}^{m} Bij\right) - \left(\frac{1}{nm}\right)*\left(\sum_{j=1}^{m} \rho j - \sum ijBij\right)$$

where, in this formula,

Cij is the sought value

Bij is the initially estimated value (n) is the number of lines of a representative matrix of a table of the refractive indices of the micro-elementary grid units (m) is the number of columns of a representative matrix of a table of the refractive indices of the micro-elementary grid units $$\sum_{i=1}^{n} Cij = \rho j$$

for all the values of i, the constraint of the column j $$\sum_{j=1}^{m} Cij = ci$$

for all the values of j, the constraint of the line i.

16. Computer program according to claim 15, wherein the following supplementary stages are carried out:
 (9) to search for a singularity C among the refractive indices calculated on completion of step (3) or adjusted on completion of step (6) or among the coefficients of attenuation calculated on completion of step (4) or adjusted on completion of step (8), and to define by referencing the grid units or the elementary micro-grid units of the singularity C with respect to a displacement guide, and
 (10) to investigate, for a plurality of points of a lens, the optical path between a starting point Aq and the singularity C regarded as the point of arrival, and to calculate a mean angle of convergence ($\sigma$) on the various investigated optical paths starting from different points of the lens and obeying a symmetry condition with respect to a laser beam caused to converge at a focal point of a neutral axis of the lens, so as to adjust a focal length at a virtual focal point determined by the angle of convergence assuming that the laser beam travels in air, in such a way as to focus the laser beam on a virtual focal point so that the singularity C coincides with a real focal point that can be destroyed, for example by vaporisation, under the action of repeated pulses of the light laser.

\* \* \* \* \*